US010147918B2

(12) United States Patent
Perez Lopez et al.

(10) Patent No.: US 10,147,918 B2
(45) Date of Patent: Dec. 4, 2018

(54) RETARDING MECHANISM

(71) Applicant: The Gillette Company, Boston, MA (US)

(72) Inventors: Cirilo Javier Perez Lopez, Eschborn (DE); Ulrich Fandrey, Wetzlar (DE); Michaela Mueller, Kronberg (DE); Andreas Erndt, Kelkheim (DE); Sebastian Hottenrott, Idstein (DE); Philipp Berger, Bad Vilbel (DE)

(73) Assignee: The Gillette Company LLC, Boston, MA (US)

( * ) Notice: Subject to any disclaimer, the term of this patent is extended or adjusted under 35 U.S.C. 154(b) by 658 days.

(21) Appl. No.: 14/224,382

(22) Filed: Mar. 25, 2014

(65) Prior Publication Data
US 2014/0295236 A1    Oct. 2, 2014

Related U.S. Application Data

(60) Provisional application No. 61/805,348, filed on Mar. 26, 2013.

(51) Int. Cl.
*H01M 2/10* (2006.01)
*B26B 21/52* (2006.01)
*A61C 17/16* (2006.01)

(52) U.S. Cl.
CPC ......... *H01M 2/1022* (2013.01); *B26B 21/526* (2013.01); *B26B 21/528* (2013.01); *H01M 2/1055* (2013.01); *A61C 17/16* (2013.01)

(58) Field of Classification Search
CPC ..... B26B 21/526; A61C 17/16; A61C 17/224; A61C 17/225
See application file for complete search history.

(56) References Cited

U.S. PATENT DOCUMENTS 4,943,498 A    7/1990    Cooper et al.
5,430,967 A    7/1995    Woodman, III et al.
(Continued)

FOREIGN PATENT DOCUMENTS

JP    63181788    7/1988
JP    2002369983    12/2002

OTHER PUBLICATIONS

Machine translation of JP 2002-369983 from Google patents printed Mar. 20, 2017.*

(Continued)

*Primary Examiner* — Maria Laios
(74) *Attorney, Agent, or Firm* — Joanne N. Pappas; Kevin C. Johnson

(57) ABSTRACT

A novel retarding mechanism is shown to reduce the inertia of the battery shell during a linear detachment movement from a handle of an appliance, such as a battery powered razor or shaver. The retarding mechanism is based on the interaction between the battery shell found on a lower portion of a razor handle and a battery carrier found within the upper portion of a razor handle. Specifically, an engagement spring having at least one knob type structure is mounted on an interior surface of the battery shell and axially engages protrusions and/or recesses on an exterior surface of the battery carrier during a detachment movement of the battery shell. During opening or detachment of the shell, the engagement of the knob with protrusions produces a retarding force effect of the shell during the linear detachment.

21 Claims, 12 Drawing Sheets

(56) References Cited

U.S. PATENT DOCUMENTS

| | | | | |
|---|---|---|---|---|
| 5,544,415 | A * | 8/1996 | Huang | B26B 19/06 30/210 |
| 7,637,014 | B2 * | 12/2009 | Schnak | B26B 21/38 30/44 |
| 7,694,419 | B2 | 4/2010 | Diehl et al. | |
| 8,037,608 | B2 | 10/2011 | Schnak et al. | |
| 2006/0246347 | A1 * | 11/2006 | Diehl | A61C 17/225 429/97 |
| 2007/0050996 | A1 | 3/2007 | Schnak et al. | |
| 2007/0050997 | A1 | 3/2007 | Schnak et al. | |
| 2008/0304258 | A1 * | 12/2008 | McMillan | F21L 4/027 362/202 |

OTHER PUBLICATIONS

PCT International Search Report with Written Opinion in corresponding Int'l appln. PCT/US2014/031733 dated Aug. 4, 2014.

* cited by examiner

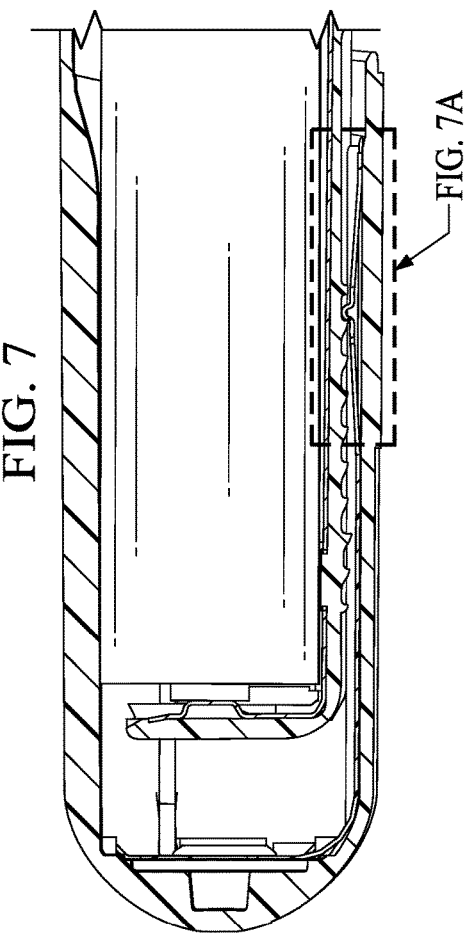
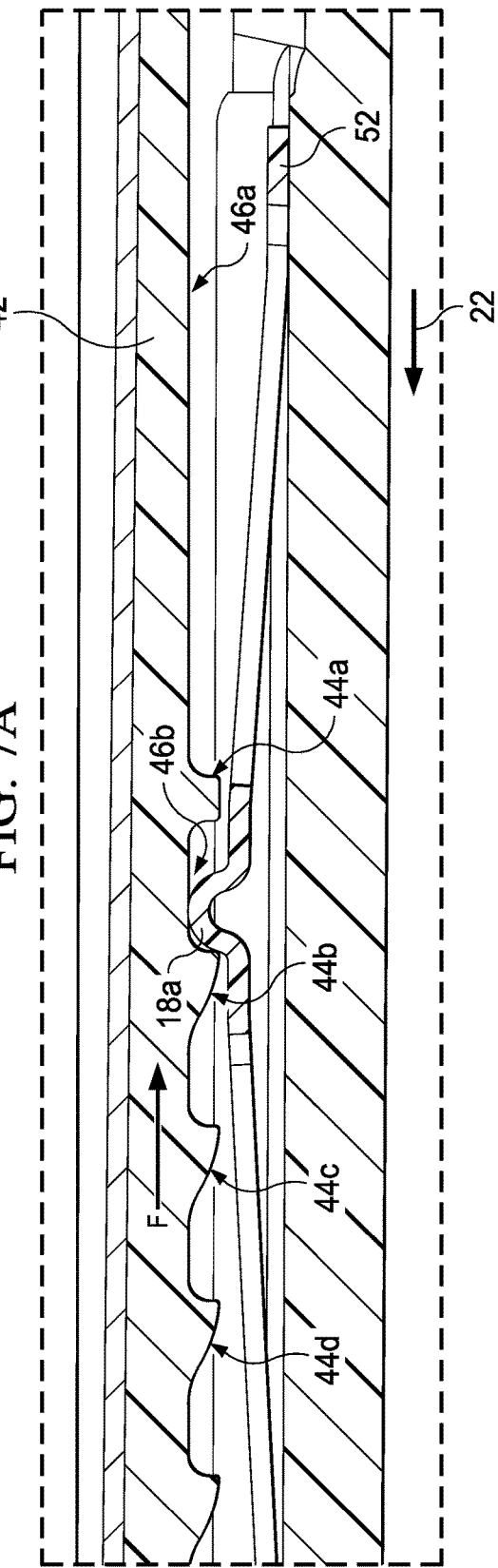

RETARDING MECHANISM

FIELD OF THE INVENTION

This invention relates to powered or battery-operated appliances, such as small consumer appliances, and more particularly to covers used in such appliances.

BACKGROUND OF THE INVENTION

In many small battery-operated devices, the batteries are replaceable by the user, and are inserted and removed from a battery compartment through an opening or carrier having a cover or shell. It is necessary to mechanically secure the cover in place, in many instances so that the batteries do not fall out, or so that the cover does not inadvertently fall off. It is also typically necessary to make electrical contact between the batteries and the electrical circuit within the device.

During the detachment of a cover or a shell from a handle of the appliance, (e.g., a razor handle) the force that the consumer has to exert to detach the shell produces significant inertia of the shell and this in turn reduces the control the consumer has of the shell and/or the battery.

A mechanism is needed to provide better control of the battery shell during its detachment or release movement from a handle, so as to reduce the inertia of the battery shell and provide the consumer with a much more pleasant operational experience.

SUMMARY OF THE INVENTION

In accordance with the invention, a powered appliance includes a handle comprising an upper part and a lower part, the lower part comprising a battery shell with one or more engagement members wherein the battery shell is retarded when detached from the upper part of the handle. In a further aspect of the invention, each of the one or more engagement members comprise one or more engagement springs which may include one or more knobs. The at least one knob may have a first curved profile. A battery carrier is included in the handle having one or more engagement structures. The one or more engagement springs and the one or more engagement structures are axially aligned along a longitudinal axis of the handle. The one or more engagement structures further comprises one or more protrusions, one or more recesses, or any combination thereof wherein each of the protrusions has a second curved profile and each of said one or more recesses has a third recessed surface. The at least one knob is engaged with one or more recesses, one or more protrusions, or any combination thereof. The first curved profile of the at least one knob is engaged with the second curved profile(s) of the one or more protrusions, the third surfaces of the recesses, or any combination thereof.

In another aspect of the invention, the battery shell traverses linearly along a longitudinal axis of the handle during detachment. This retarded detachment provides a force against battery shell movement. Generally the retarded detachment is provided by the one or more engagement members or springs remaining in contact with the one or more engagement structures.

In other aspects of the invention, the engagement member is comprised of metal, does not provide electrical contact with a battery disposed in the battery carrier, and is secured to the battery shell. Also, in the present invention, the battery shell does not serve to retain a battery in the handle. A battery disposed in the battery carrier drives power to a component such as a motor of the appliance.

In further aspects of the invention, the at least one knob has a height ranging from about 0.3 mm to about 0.7 mm and a radius ranging from about 0.3 mm to about 0.6 mm, or any combination thereof, the protrusions have a height ranging from about 0.2 mm to about 0.6 mm, a radius ranging from about 0.04 mm to about 0.5 mm, and a distance between a first protrusion and a second protrusion ranging from about 1.5 mm to about 2 mm, or any combination thereof.

In yet further aspects, the at least one knob is disposed on an elongated arm portion of the one or more engagement members, wherein adjacent said at least one knob is at least one flat area and wherein the arm portion comprises at least one angled portion, the at least one angled portion comprises an aperture.

The powered appliance of the present invention may be a razor, toothbrush, facial device, or flashlight.

In yet another aspect of the present invention, the appliance comprises a handle with at least one engagement spring in one part of the handle and an engagement structure in another part of the handle, the engagement spring and the engagement structure when coupled together retarding detachment of one part of the handle from the other.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIGS. 7 and 7a are close-up views of FIG. 6 depicting the force against the battery shell movement in accordance with the present invention.

FIGS. 9 and 9a depict a preferred geometry of the knob of the engagement spring in accordance with the present invention.

DETAILED DESCRIPTION OF THE INVENTION

The novel retarding mechanism of the present invention reduces the inertia of the battery shell during a linear detachment movement from a handle of an appliance, such as a battery powered razor or shaver.

The present invention does not generally describe how to maintain the battery itself fixed in its battery compartment or carrier with a battery shell in its closed position. The present invention also generally focuses on a cover or battery shell being detached or displaced along a linear direction of the handle, (e.g., the battery shell moving along or in the direction of the longitudinal axis of the handle). This detachment or release traversal direction generally differs from appliances with battery shells that generally are detached by moving in a non-linear, rotational or transversal direction or those where the battery shell includes a threaded connection or bayonet mechanism (e.g., many battery-powered wet razors).

For instance, focusing on a powered wet razor type of appliance, it is noted that the present invention's retarding mechanism is based on the interaction between the battery shell (on a lower portion of a razor handle) and the upper portion of a razor handle, namely that of the presence of an engagement member having a spring mounted on an interior surface of the battery shell which engages the exterior surface or an engagement structure of the battery carrier during a detachment movement of the battery shell, this thereby producing a retarding or hold back effect of the shell during the detachment. As noted above, the present invention may generally involve a linear direction of detachment along a longitudinal axis of the razor.

The retarding mechanism of the present invention is based on the interaction between the engagement structure molded on the battery carrier and the engagement feature on the engagement spring. During the displacement of the battery shell, the engagement spring offers a resistance that is a function of its preload compression, its spring constant and the geometry of the battery carrier structure, and depending of the intensiveness of that resistance, the retarding effect will be larger or smaller.

The term "spring" as used herein, signifies any type of mechanical spring, such as a compression spring, a leaf spring, or any feasible spring or combination thereof.

The terms "knob", "protrusion", "recess", as used herein may be any size structure of any geometrical shape, e.g., having a curved or linear profile or any feasible combination thereof.

The term "flat" or "flat areas" as used herein may signify a surface that is horizontally level, generally not slanted, even, or without marked projections or depressions.

The term "angled" as used herein may signify a surface that has an angle or angles, is disposed at a slant or bent at an angle, which may or may not be linear.

Figure 1:
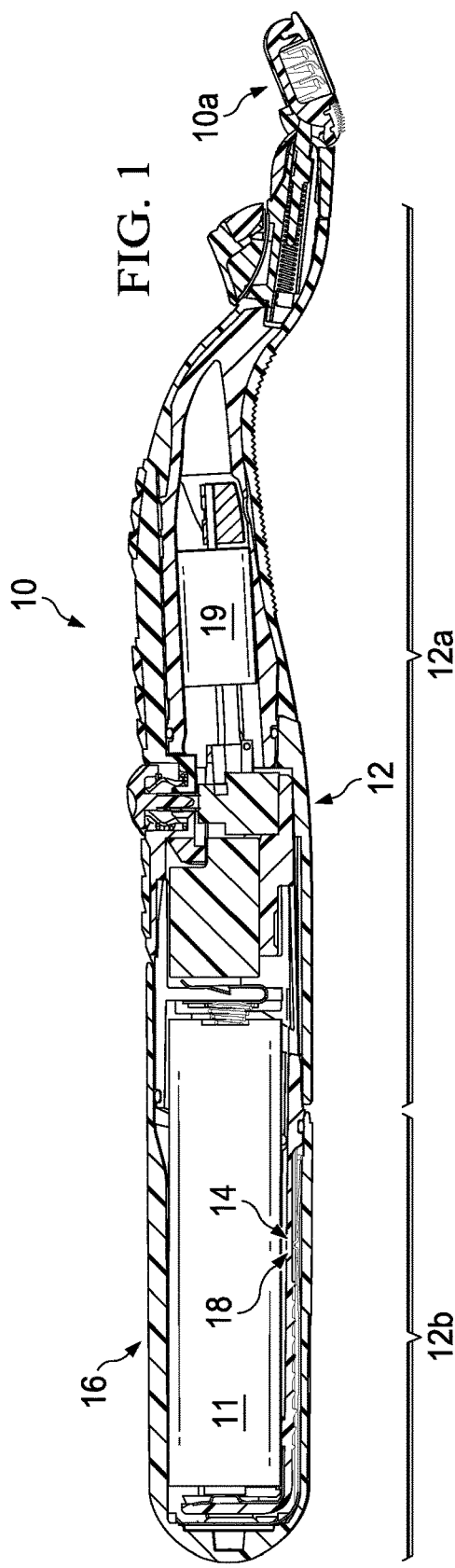
FIG. 1 is a cross-sectional view of a powered wet razor handle having an engagement member and engagement structure in accordance with the present invention.

Referring to FIG. 1, an exemplary powered appliance 10 in accordance with the present invention, namely that of an assembled powered wet razor is shown. While a razor is being used and depicted as an example of a type of powered appliance contemplated by the present invention, the present invention is not limited to razors and may include any other battery powered appliances, such as toothbrushes, facial devices or appliances such as exfoliation devices or skin brushes, or other cosmetic applicators, flashlights and other commonly known small consumer powered appliances.

The razor 10 is shown to include a razor cartridge 10a coupled to a handle 12. Handle 12 includes several components. The handle 12 generally has an upper portion 12a and a lower portion 12b. The upper portion 12a includes a battery carrier 14 within the handle 12, a battery 11 disposed and held within the battery carrier 14, a battery shell 16 at the bottom portion 12b of the handle 12 serving to cover or encase the battery carrier 14 inside the handle and to provide a bottom to the handle, and one or more engagement members 18 within the battery shell 16.

Engagement members are preferably comprised of at least one spring. An electrical connection is established between the battery 11 and a motor 19 found within the handle. Once this electrical connection is established the motor is powered and provides vibration that is transmitted to the handle and then desirably transmitted to a razor cartridge 10a or in other appliance types, for powering or driving a vibrating function of any other component (e.g., brush head).

It should be noted however, that the spring 18 itself does not provide the electrical contact needed to provide power to the razor. In fact, in the present invention, the placement of a battery 11 in the battery carrier 14 on an upper portion of the handle is all that is generally necessary to provide power to the razor; neither the battery shell nor the spring in the lower portion of the handle is necessary for powering up the razor.

The handle 12, including battery shell 16, as shown are generally formed in an oval, elliptical shape, though any shape is contemplated for these components in the present invention such as, for instance, a generally cylindrical shape. The battery carrier 14 may also be an oval, elliptical shape to fit or guide easily within the shell 16 and handle 12. Though good guidance may be provided between the parts when they are similarly shaped, the shell and the carrier may be of different shapes (e.g., one may be oval and one may be cylindrical) and still achieve such good guidance.

While most of the handle components are generally made of a plastic material, engagement spring 18 may desirably be comprised of metal in the present invention. The engagement spring 18, as shown, may desirably be a compression type spring.

Figure 2:
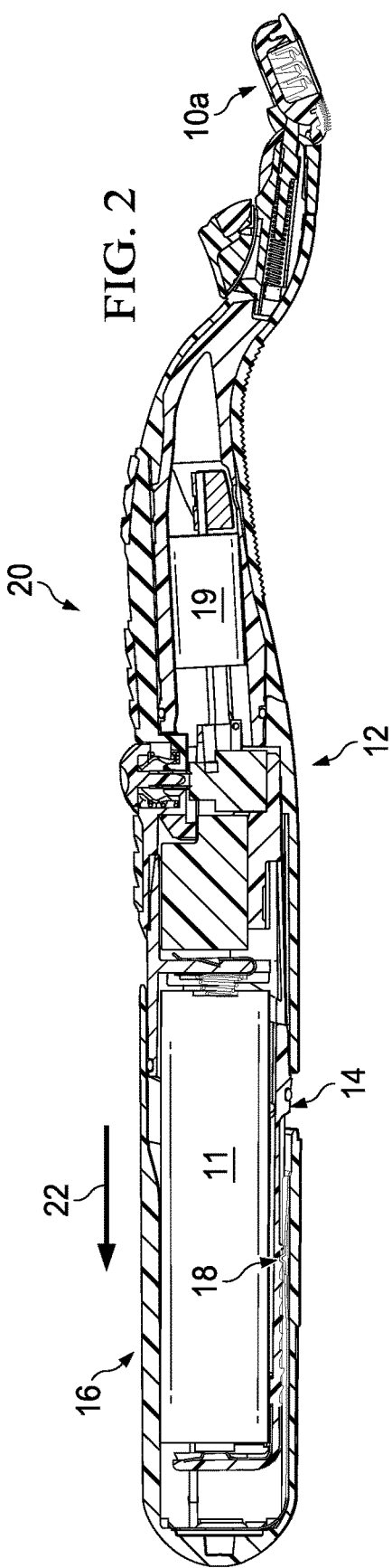
FIG. 2 is a cross-sectional view of a powered wet razor handle of FIG. 1 as the battery shell is detached longitudinally in accordance with the present invention.

To remove the battery 11 from the handle 12 or to open the razor handle for any reason, one has to take off, detach, or release the battery shell 16 along a longitudinal direction as indicated by arrow 22 in FIG. 2.

The engagement spring 18 within the battery shell 16 may desirably include one or more knobs. An embodiment with one knob 18a is shown in FIGS. 3a and 3b and an alternate embodiment with two knobs is shown in FIG. 11. Shown in FIGS. 3 and 5-8 of the present invention, an engagement spring 18 comprising one knob 18a is disposed within the battery shell 16.

Figure 3:
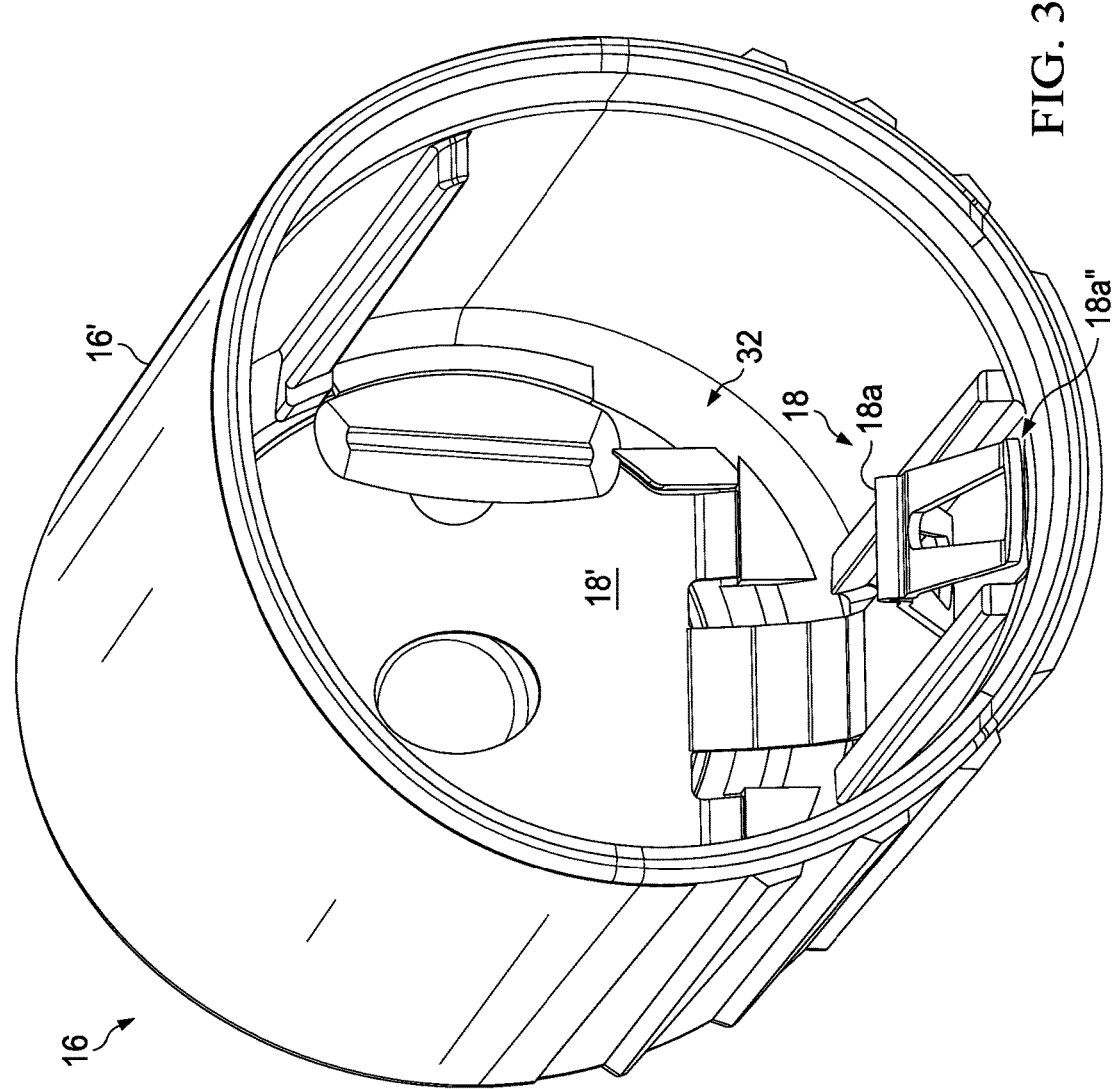
FIG. 3 is a close-up diagrammatical view of the battery shell of FIG. 1.
Figure 3A:
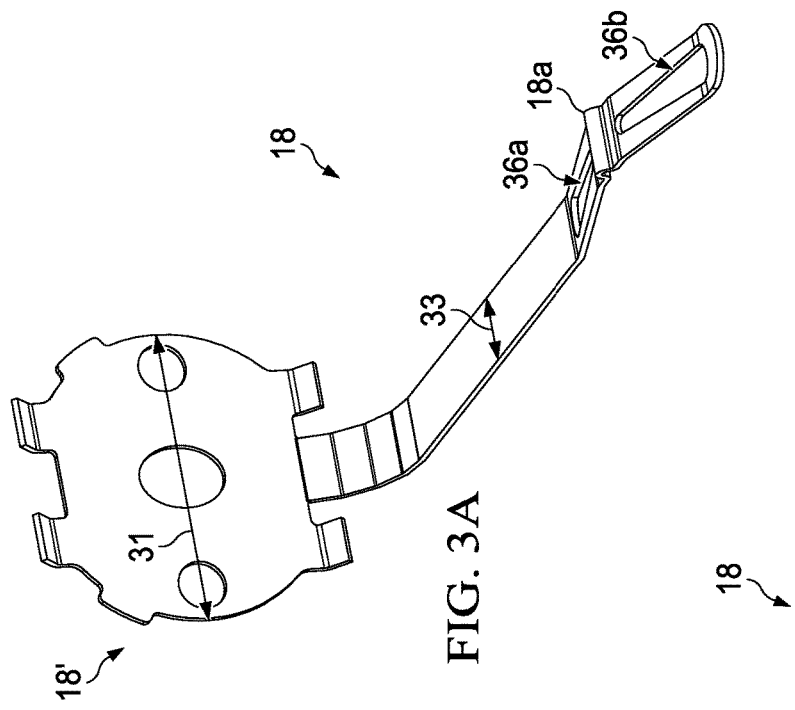
FIGS. 3a and 3b are perspective and side views of the engagement member of the present invention.
Figure 3B:
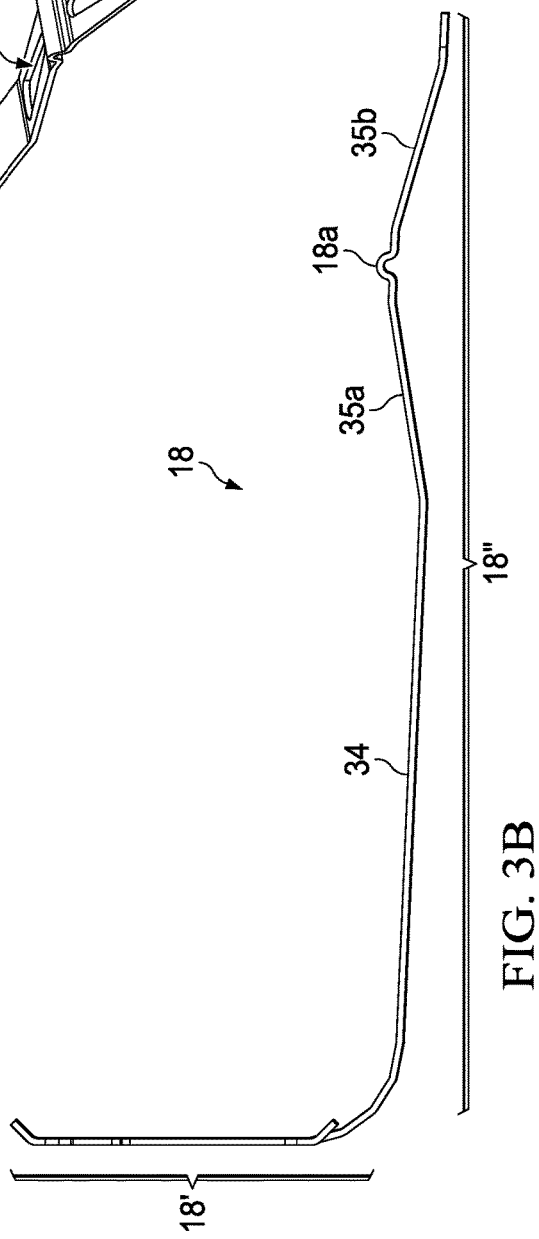

One or more portions of the engagement spring 18 may be fixed into a bottom interior end portion 32 of the battery shell 16 as shown in FIG. 3. As clearly depicted in FIGS. 3, 3a and 3b, the engagement spring 18 has a generally circular portion 18' that is secured to the interior surface 32 of the bottom end 16' of the battery shell 16 and at least one arm portion 18" extending from the circular portion 18', in a longitudinal direction away from the bottom end 32 generally along the axis of the handle. The circular portion 18' may be mounted or fixed to the battery shell by an interference fit, ultrasonic welding, or any feasible securing or fastening technique, or combination thereof.

In FIG. 3a, the circular portion 18' is shown having a width dimension 31 of preferably about 8 mm to about 10 mm, and more preferably about 9.15 mm and the arm portion 18" having a width dimension 33 of preferably about 1.5 mm to about 2.5 mm, and more preferably about 2 mm.

As shown in FIG. 3b, arm portion 18" may desirably include a linear portion 34 and angled portions 35a and 35b straddling knob 18a.

Angled portions 35a and 35b are generally desirably symmetrical, though asymmetrical portions are contemplated in the present invention. The linear portion 34 may desirably be about half the length of the total arm portion 18", though any feasible length is contemplated by the present invention. Generally, theoretically the longer the linear portion 34, the larger the retention force. Furthermore, providing a greater width dimension 33 of arm portion 18" may allow for flatter area or more linear-like angled portions.

The angled portions 35a and 35b may desirably each have one or more apertures 36a and 36b. As shown in FIG. 3a, angled portion 35a has one aperture 36a and angled portion 35b has one aperture 36b. While not required for the present invention, apertures 36a and 36b may generally provide some advantages such as homogenizing the strength on the angled portions 35a and 35b during the compression of the spring 18.

A more uniform distribution of the stress on the arm portion 18" may be achieved in the presence of apertures in angled portions, thereby a higher stress on the arm can be accommodated and as such, the spring may be desirably compressed with minimal permanent deformation. The size and shape of the apertures can be determined and feasibly achieved depending on the point where the stress distribution is desired. The size and shape of the apertures may be desirably small enough, so as to not interfere with the engagement structure retarding mechanism provided by the battery carrier.

Figure 5:
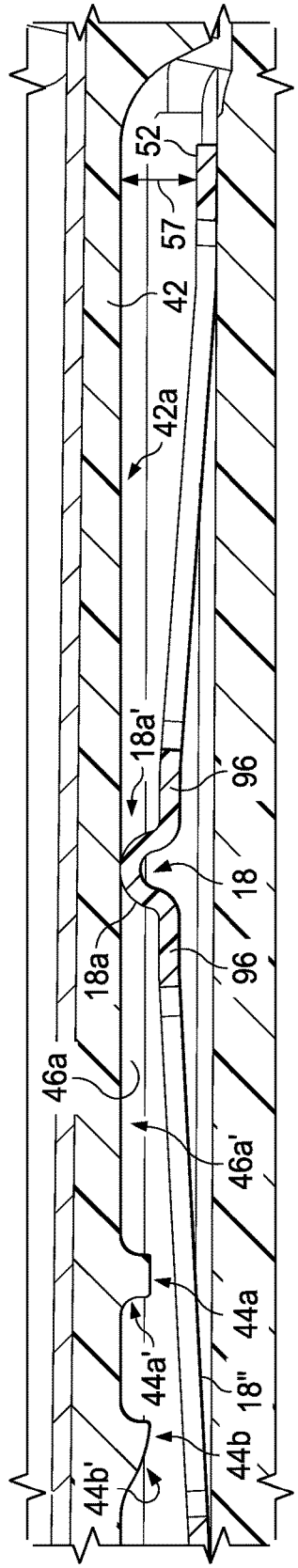
FIG. 5 is a close-up cross-sectional view of the engagement spring knob in its pre-loaded engagement position with the engagement structure in accordance with the present invention.

The engagement spring 18 may generally be considered in a preloaded compressed position when the handle is fully formed or assembled as shown in FIGS. 1 and FIG. 5, for instance.

When the battery shell 16 is secured to or mounted on the razor handle 12 providing a closed, position for the handle (e.g., the shell does not fall off the upper portion 12a of the handle 12) as shown in FIG. 1, the engagement spring arm portion 18" extends longitudinally almost the entire length of the carrier 14.

In this position, with the battery shell assembled on the battery carrier and the razor being ready for use, the razor handle is generally also waterproof.

Knob 18a of the engagement spring 18 may desirably be in direct and substantially permanent contact with at least one portion of an engagement structure 42 (FIGS. 1, 4) disposed on the battery carrier 14. The spring 18 and more particularly, at least its arm portion 18" is generally axially aligned with the engagement structure 42.

Figure 4:
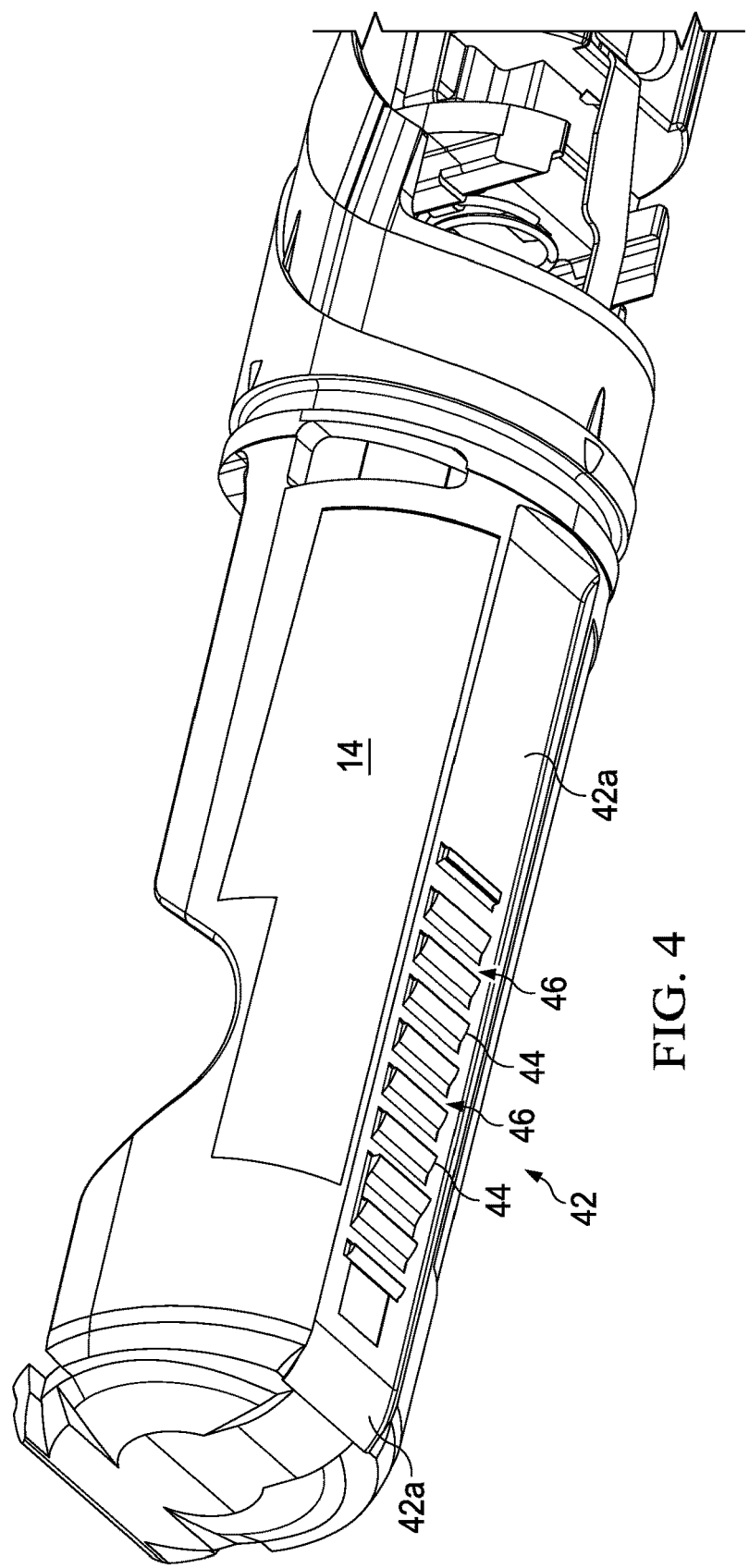
FIG. 4 is a close-up diagrammatical view of the battery carrier of FIG. 1.

The engagement structure 42, shown more clearly in FIG. 4, may be desirably integrally molded on an exterior surface 42a of the battery carrier 14. The present invention also contemplates an embodiment where the engagement structure 42 is independently formed and secured to the carrier, even comprised of a different material than the carrier. For instance, the carrier may be made of a plastic and the engagement structure may be comprised of a metal, or vice-versa.

The engagement structure 42 as shown in FIG. 4 preferably comprises one or more small protrusions 44 and one or more recesses 46 and are disposed on the carrier in a longitudinal manner so as to preferably engage with knob 18a found on the longitudinal arm portion 18" of the engagement spring 18.

FIG. 5 is a close-up cross-sectional view of the handle in a closed position such as that shown in FIG. 1. The spring has one knob 18a and the engagement structure 42 has a plurality of protrusions 44 and recesses 46 which are disposed on surface 42a and axially aligned with the arm portion 18" of the spring 18.

Figure 6:
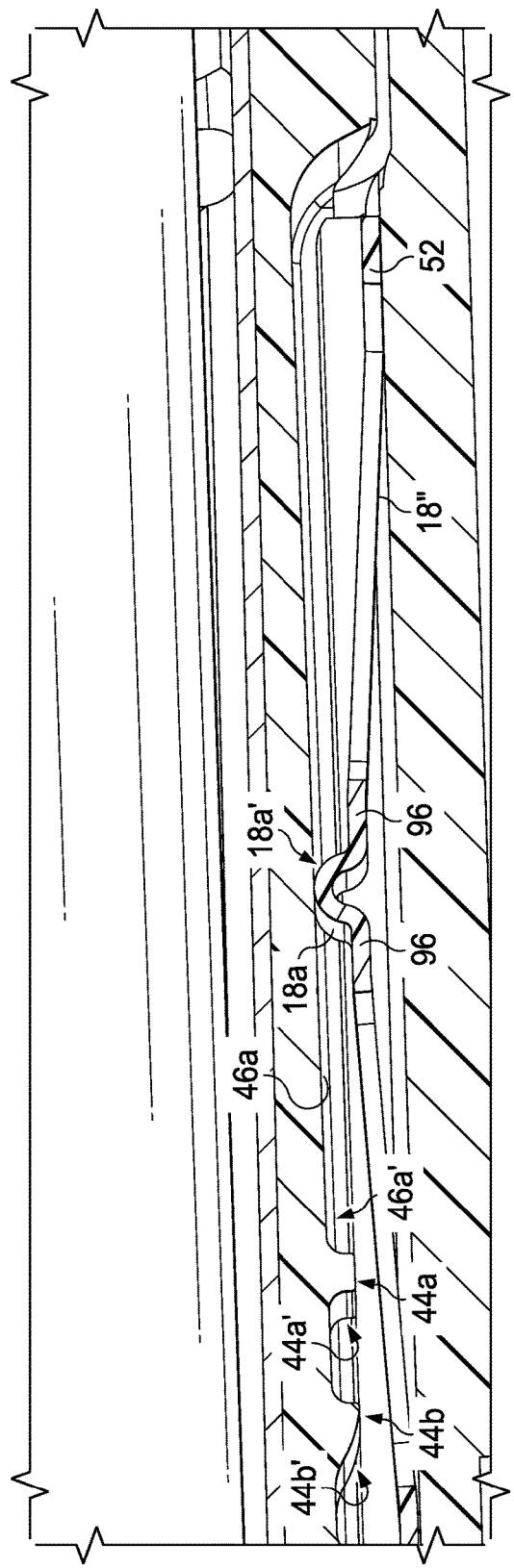
FIG. 6 is a close-up of FIG. 2's cross-sectional view of the engagement spring knob as it linearly traverses the engagement structure during detachment of the battery shell.
Figure 8:
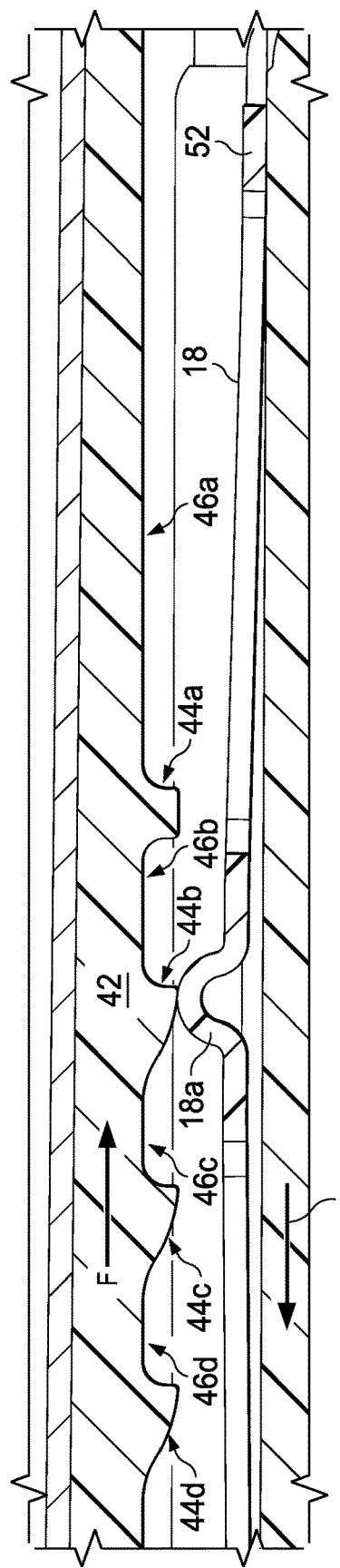
FIG. 8 is a further close-up cross-sectional view showing the engagement spring of the battery shell as it traverses further along a protrusion of the engagement structure of the battery carrier in accordance with the present invention.

FIGS. 6-8 depict a sequence of diagrams of the detachment or release of the battery shell from the handle. As the shell 16 is initially linearly detached (released or removed from the handle portion 12a), the spring knob 18a moves linearly along the engagement structure 42 of the battery carrier 14. During the detachment movement of the battery shell, the small engagement spring knob 18a finds on its way, a first recess 46a (shown in FIG. 6), then a first small protrusion 44a (shown in FIG. 6-7) of the engagement structure 42 of the carrier 14 which generally provide a force F (shown by force arrow F in FIG. 7) or resistance to spring 18's longitudinal movement, providing a more controlled detachment of the shell from the handle. In a continued detachment of the battery shell 16, the engagement spring knob 18a finds on its way, a second recess 46b, and then a second small protrusions 44b of the engagement structure 42 of the carrier 14, and so on.

This force F is generally applied in an opposite direction from or against the battery shell movement as indicated by force arrow "F" in FIG. 7. Since the engagement spring 18 is mounted on the battery shell 16, the spring 18 is affected directly as well by force F and it is this resistance that supplies the basic principle of the present invention acting as a retarding mechanism.

As shown in FIGS. 6-9, knob 18a of the engagement spring 18 may generally overcome each of the one or more protrusions 46 of the engagement structure 42 on the carrier 14 in major part due to the flexibility of the engagement spring 18 and the curved outer surface or profile 18a' of the knob 18a. During retardation, the curved profile 18a' of knob 18a is engaged and generally remains in contact sequentially with each of the individual curved profiles 44a', 44b', 44c', etc. of the one or more protrusions 44a, 44b, 44c on the engagement structure 14 and the recess surface 46a', 46b', 46c', etc. of the one or more recesses 46a, 46b, 46c, etc. of the engagement structure 14, or any combination thereof.

Several parameters may assist in providing optimal performance of the mechanism of the present invention. The resistance or force F that desirably retains the engagement spring 18 is a function of many parameters, for instance, the material and geometry of the engagement spring, the finishing surfaces of the areas in contact, which may generally have an effect on the coefficient of friction, the pre-load compression of the engagement spring, the geometry of the knob(s) on the engagement spring and the geometry of the protrusion(s) and recesses on the engagement structure.

The type of engagement spring material chosen is generally important for its ability to provide a flexible or elastic performance. In addition, as mentioned above, the spring is desirably comprised of metal to provide a durable, long-lasting engagement member.

In one preferred embodiment, the spring is comprised of any type of hard metal. A generally desirable type of metal in the present invention may, though would not be limited to, have a hardness characteristic based on a German industry norm (DIN) or standard, for instance, a DIN number of about 1.4310+C1150 with a tensile strength range from about 1150 N/mm$^2$ to about 1300 N/mm$^2$. If desired, it may be tempered to potentially achieve an even higher tensile strength. By tempering, generally about a 10 to about 20 percent improvement in tensile strength may be predictably achieved. It is possible that a different type of metal may be chosen having a hardness at a DIN number of about 1.4310+C1300 (e.g., SUS 301-H) to generally provide a similar tensile strength from about 1300 N/mm$^2$ to about 1500 N/mm$^2$ (+C1300). As with +C1150, this may or may not be provided with a further tempering process.

Figure 9:
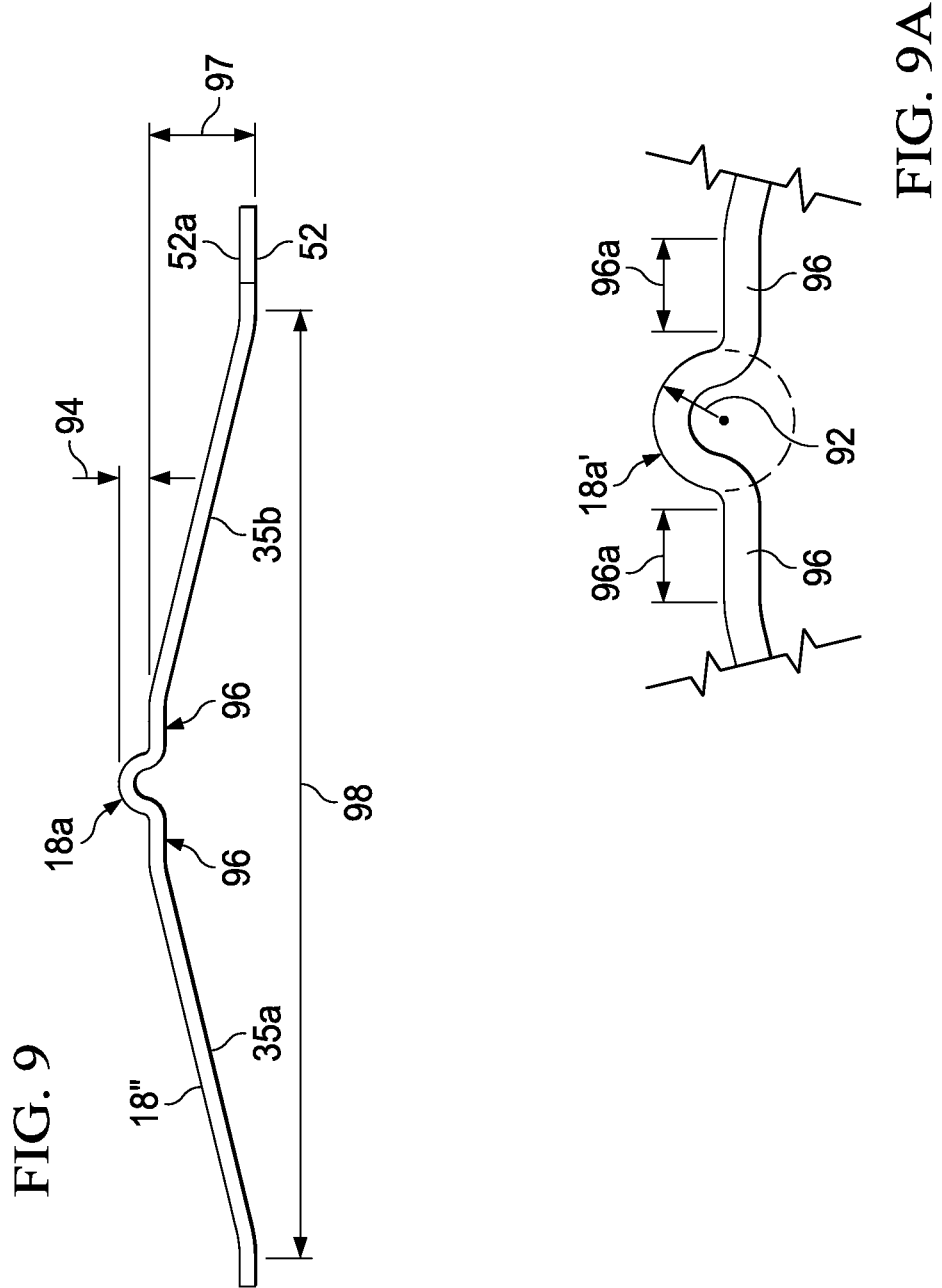

As indicated in FIGS. 9 and 9a, the geometry of the knob of the engagement spring 18 may desirably provide an optimal retarding effect. A desired radius 92 of the knob 18a may preferably be in the range of about 0.3 mm to about 0.6 mm, and more preferably at about 0.4 mm. A desired height 94 of the knob may preferably be in the range of about 0.3 mm to about 0.7 mm, and more preferably at about 0.4 mm.

In addition, an optimal length 98 for arm portion 18" may preferably be in the range of from about 12 mm to about 15 mm, and preferably about 13 mm.

The arm portion 18" may have a bend at the location of the knob (as shown by two angled portions flanking the knob in FIG. 9) or alternatively, may be disposed in another non-linear formation or a substantially straight line. The distal end 52 (shown in FIGS. 5-9) of the spring 18 is generally desirably a free end and not secured to any other component. The present invention however also contemplates that the arm portion 18" or its end may be guided, or partially or totally fixed. The height 97 of the spring 18 from about a top surface 52a of the end 52 to the flat area 96 is preferably about 1 mm to about 1.7 mm and preferably about 1.4 mm. The height 97, unlike height 57, generally represents the physical height of the spring when it is not compressed (e.g., when the engagement member is not yet mounted on the battery shell).

Moreover, in FIG. 9, the one or more flat areas 96 shown may be disposed on either side or both sides of the knob and are generally formed in this manner to avoid deformations of the knob during the compression movement of the engagement spring 18 as any knob deformations may likely produce an undesirable reduction in the retention force F. With two flat areas 96 present, better stress distribution is provided thereby generally minimizing these deformations. A desirable length 96a for each flat area 96 may preferably be in the range of from about 0.8 mm to about 1.2 mm, and more preferably at about 1 mm. In general, the arm portion or spring may desirably be more mechanically robust, the shorter the flat area length.

The pre-load compression of the engagement spring which serves to provide an optimal retention force and minimal engagement spring deformation may be related to the height of the engagement spring and the relative position of the engagement protrusion on the battery carrier surface 42a. In the present invention, the optimal pre-loaded or compressed height 57 may preferably be about 0.8 mm to about 1.2 mm, and more preferably about 1.1 mm as indicated in FIG. 5. This pre-load height 57 as shown may desirably generally be the height from the end's top surface 52a to about the top of the knob's curved profile 18a' and represents the status of the spring when the battery shell 16 is connected or assembled with the carrier 14 and the knob 18 of the spring 18 is located in one of the recesses 46.

Figure 10:
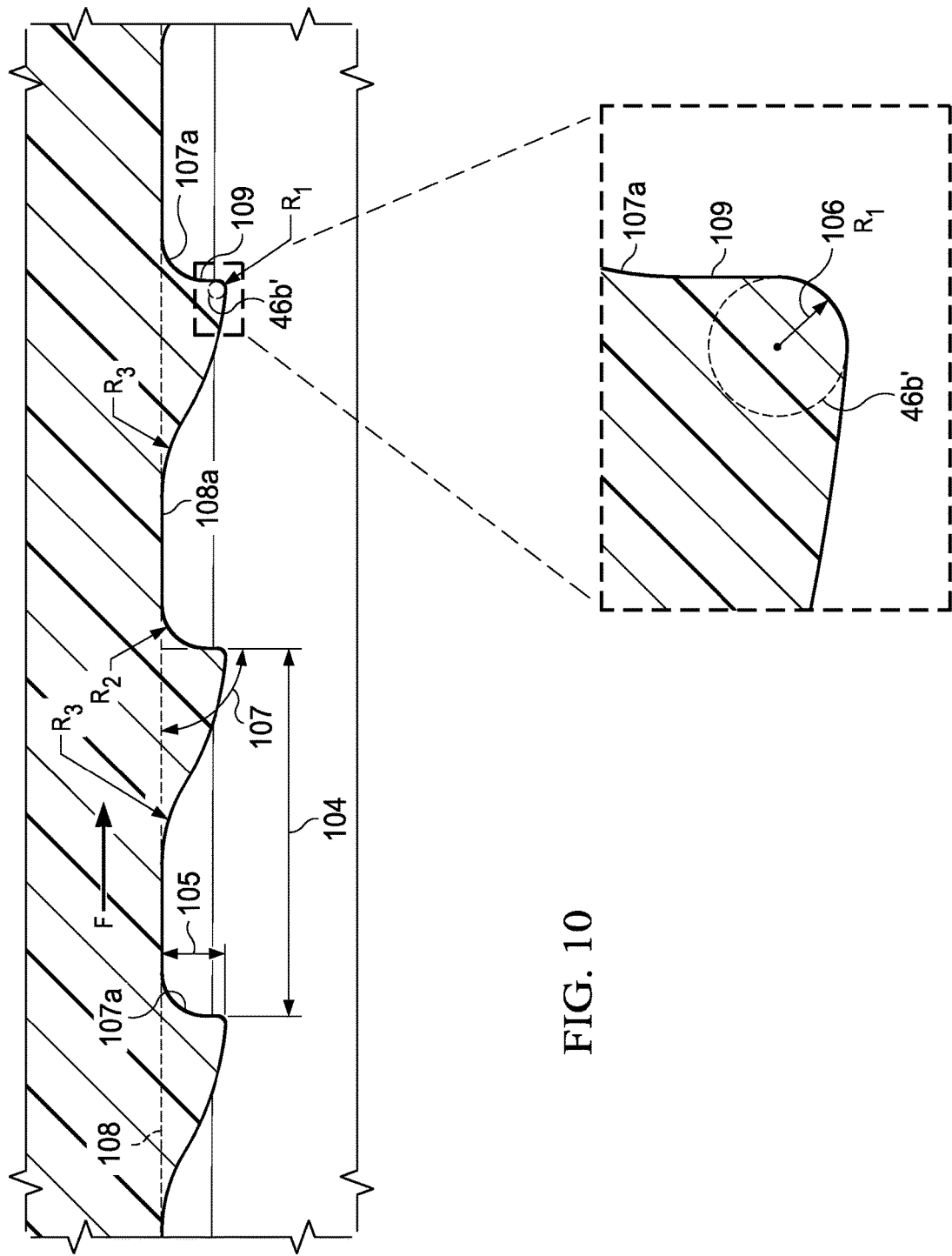
FIG. 10 depicts a preferred geometry of the protrusions of the engagement structure in accordance with the present invention.

As indicated in FIGS. 10 and 10a, the distance 104 generally between protrusions 44 on the battery carrier 14 may preferably range from about 1.5 mm to about 2 mm, and more preferably about 1.7 mm. A radius dimension 106 of a protrusion 44 may preferably range from about 0.04 mm to about 0.5 mm, preferably about 0.4 mm, and more preferably about 0.08 mm. The height 105 of the protrusion 44 may preferably range from about 0.2 mm to about 0.6 mm, and more preferably about 0.3 mm. It should be noted that not all protrusions, or recesses, on an engagement structure of a battery carrier have to be identical, or have identical dimensions, as any geometry per protrusion and/or recess, and any spacing therebetween is contemplated in the present invention. The height 105 may desirably be determined as the distance of the straight line from point R1 at the tip of the protrusion to a base point R2 or R3 of the protrusion. If the base points of the protrusions are not on a horizontal line than the height may be determined from the furthest base point from the tip point R1.

As indicated in FIG. 10, a "flank" angle 107 is shown as being about 90°. In accordance with the present invention, the angle that is shaped by the flank 107a of the protrusion and a horizontal line 108 that the protrusions generally lie upon, ranges from about 60° to about 90°, preferably 70°, and more preferably about 80°, and most preferably about 90°. The flank line 109 may desirably be defined on the flank 107a of the protrusion as a straight line from point R1 at the tip of the protrusion toward point R2 at the base area 108a of the protrusion. As shown in FIG. 10, flank line 109 is a straight line perpendicular to horizontal line 108. Flank angle 107 may desirably be determined by the angle formed from tip R1 to tip R3 at the other base point of the protrusion (e.g., akin to R2 on the other side of a base 108a of the protrusion). Generally, horizontal line 108 of the protrusions may be substantially parallel to the engagement spring (not shown) of the present invention.

Generally, the flank angle and the engagement force F are directly related, such that a higher angle may provide a higher engagement force and a lower angle may provide a lower engagement force. A maximum force may thus be obtained with the flank angle 107 being at about a 90° angle. If the angle is higher than 90°, a risk may arise of damaging the engagement spring of the present invention.

Figure 11A:
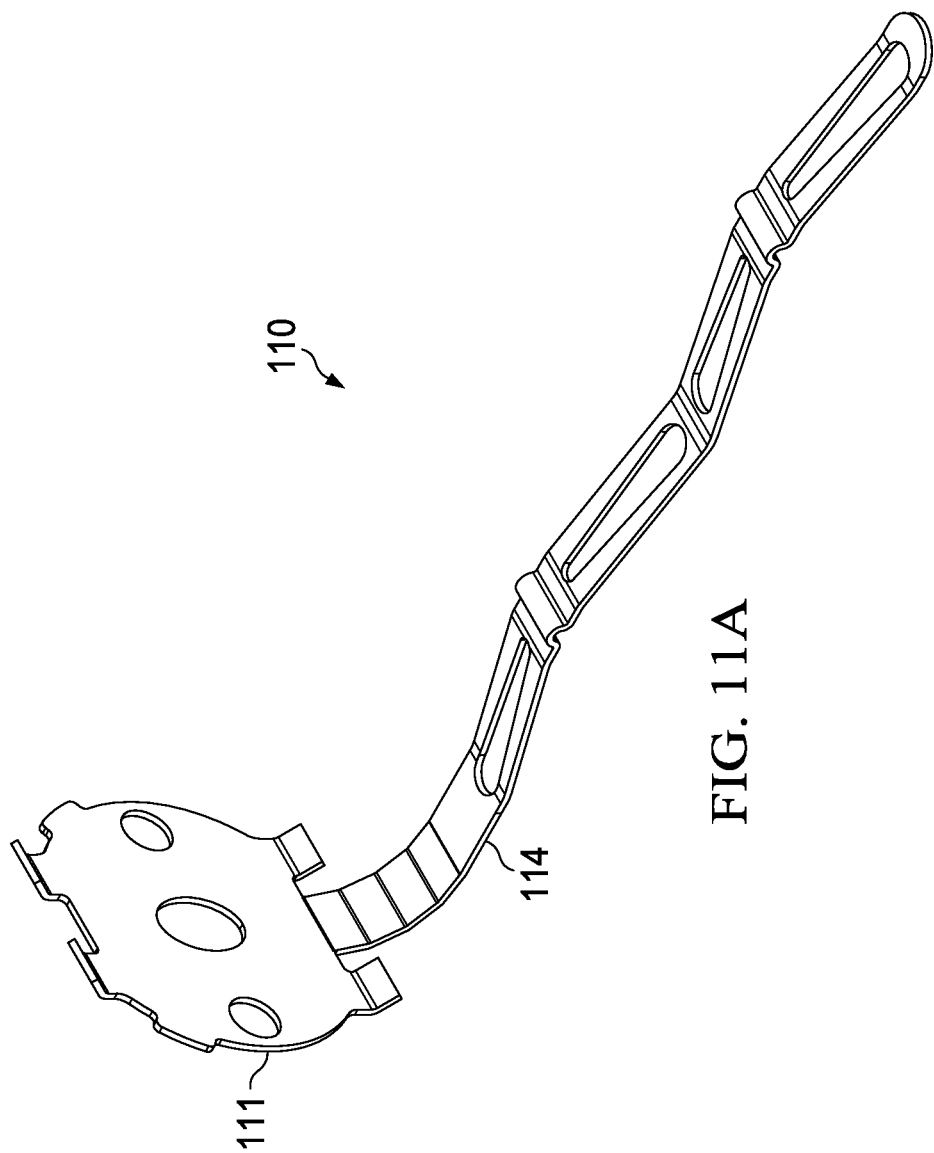
FIGS. 11a, 11b, and 11c are perspective, top and side views, respectively, of an alternate embodiment of the engagement member of the present invention.
Figure 11B:
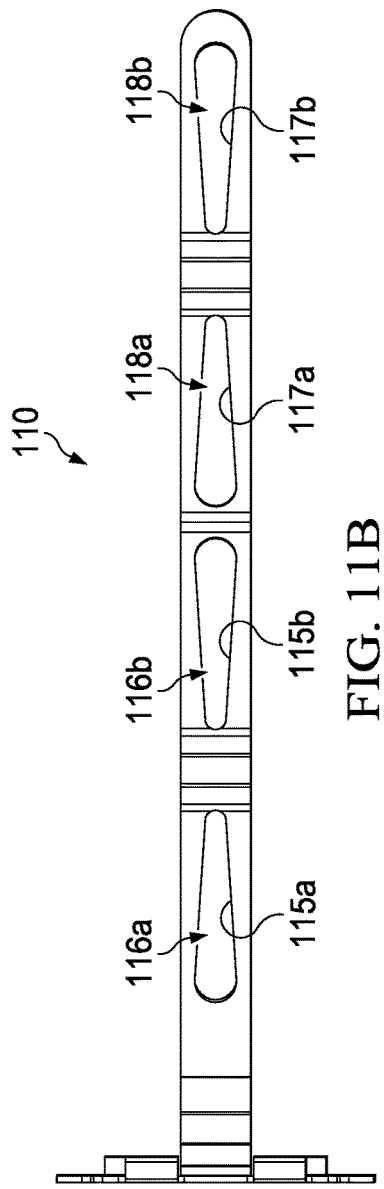
Figure 11C:
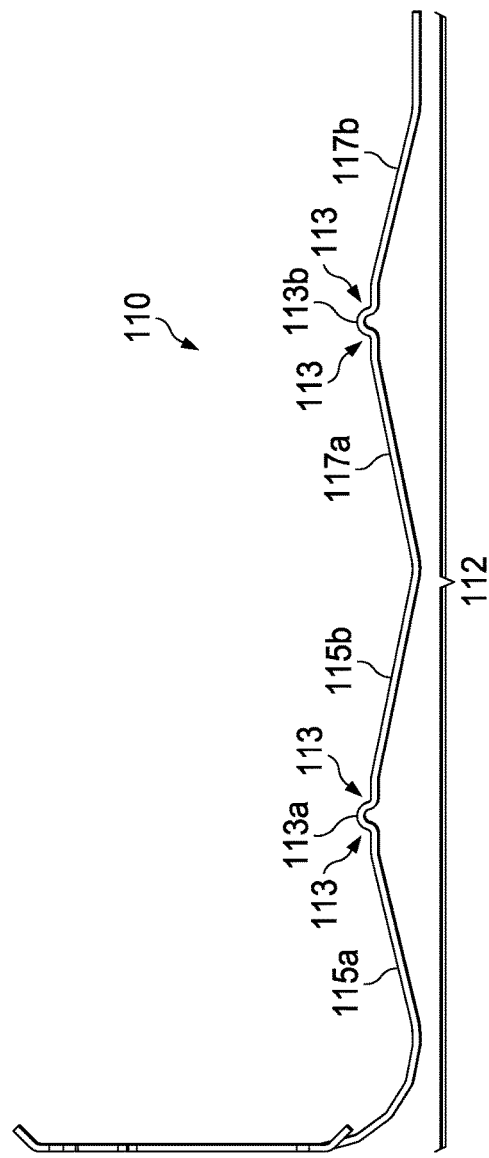

Referring to FIGS. 11a, 11b, and 11c, alternate embodiment views for engagement member 110 of the present invention are depicted. In FIG. 11, a circular portion 11 is provided having an arm portion 112 extending therefrom. The arm portion 112 may or may not be provided with one linear portion 114 and also may generally have at least two knobs 113a and 113b and angled portions on either side of these two knobs. As shown, the angled portions are symmetrical or have a similar length and angle, though as described above with regard to the FIGS. 3a, 3b, asymmetrical angled portions are also feasibly contemplated in the present invention.

As shown in FIG. 11b, angled portions 115a, 115b, 117a, 117b may each have one aperture 116a, 116b, 118a, 118b disposed therein, the apertures being of the type described herein. Further, as shown in FIG. 11c, one or more flat areas 113 are disposed immediately adjacent each knob.

Figure 12:
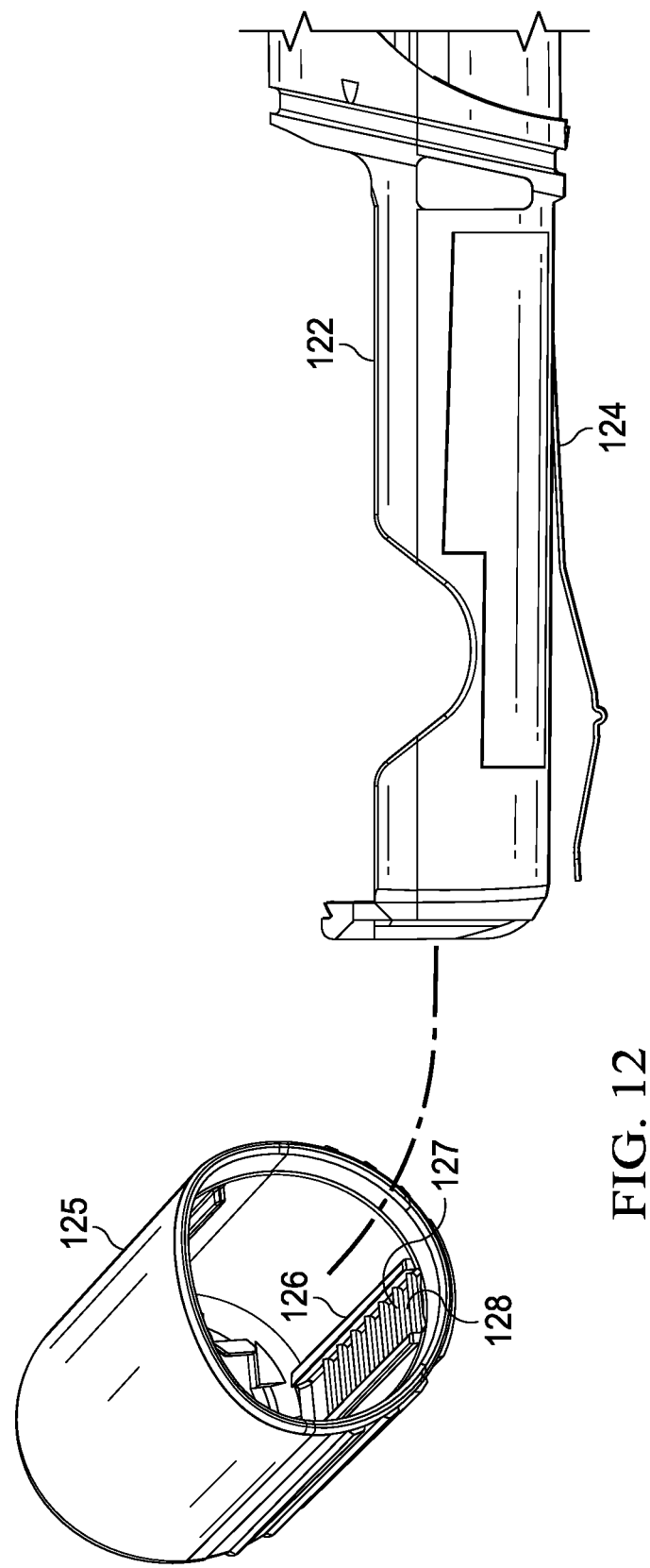
FIG. 12 depicts an alternate embodiment of the present invention where the battery carrier comprises an engagement structure and a battery shell comprises an engagement member having a spring.

FIG. 12 depicts an alternate embodiment of the present invention where the battery carrier 122 comprises an engagement member 123 with one or more springs 124 and the battery shell 125 comprises an engagement structure 126 with one or more protrusions 127 and/or one or more recesses 128. The interconnection and functionality of engagement member 123 and engagement structure 126 theoretically is generally similar to the functionality thus far described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A powered appliance comprising: a handle comprising an upper part and a lower part, the lower part comprising a battery shell with one or more engagement members wherein each of said one or more engagement members comprise one or more engagement springs, the upper part comprising a battery carrier having one or more engagement structures, said engagement structures comprising one or more protrusions, one or more recesses, or any combination thereof, wherein said one or more engagement members is engaged with said engagement structures, such that the battery shell is retarded when detached from the upper part of the handle.

2. The powered appliance of claim 1 wherein said one or more engagement springs further comprise at least one knob.

3. The powered appliance of claim 2 wherein said at least one knob has a first curved profile.

4. The powered appliance of claim 3 wherein said first curved profile of at least one knob is engaged with second curved profiles of one or more protrusions, recessed surfaces, or any combination thereof.

5. The powered appliance of claim 2 wherein said at least one knob is engaged with one or more recesses, one or more protrusions, or any combination thereof.

6. The powered appliance of claim 5 wherein said retarded detachment is provided by said one or more engagement springs remaining in contact with said one or more engagement structures.

7. The powered appliance of claim 2 wherein said at least one knob has a height ranging from about 0.3 mm to about 0.7 mm and a radius ranging from about 0.3 mm to about 0.6 mm, or any combination thereof.

8. The powered appliance of claim 2 wherein said at least one knob is disposed on an elongated arm portion of said one or more engagement members.

9. The powered appliance of claim 8 wherein adjacent said at least one knob is at least one flat area.

10. The powered appliance of claim 8 wherein said elongated arm portion comprises at least one angled portion.

11. The powered appliance of claim 10 wherein said at least one angled portion comprises an aperture.

12. The powered appliance of claim 1 wherein said one or more engagement members and said one or more engagement structures are axially aligned along a longitudinal axis of the handle.

13. The powered appliance of claim 1 wherein each of said one or more protrusions have a second curved profile and each of said one or more recesses has a recessed surface.

14. The powered appliance of claim 1 wherein said battery shell traverses linearly along a longitudinal axis of the handle during detachment.

15. The powered appliance of claim 14 wherein said retarded detachment provides a force against battery shell movement.

16. The powered appliance of claim 1 wherein said one or more engagement members is comprised of metal.

17. The powered appliance of claim 1 wherein said one or more engagement members do not provide electrical contact with a battery disposed in said battery carrier.

18. The powered appliance of claim 1 further comprising a battery disposed in said battery carrier to drive power to a component of said appliance.

19. The powered appliance of claim 1 wherein said one or more protrusions have a height ranging from about 0.2 mm to about 0.6 mm, a radius ranging from about 0.04 mm to about 0.5 mm, and a distance between a first protrusion and a second protrusion ranging from about 1.5 mm to about 2 mm, or any combination thereof.

20. The powered appliance of claim 1 wherein said one or more engagement members is secured to said battery shell.

21. The powered appliance of claim 1 wherein said appliance is a razor, toothbrush, facial device, or flashlight.

* * * * *